(12) United States Patent
Ogata et al.

(10) Patent No.: US 12,313,972 B2
(45) Date of Patent: May 27, 2025

(54) RESIST UNDERLAYER FILM-FORMING COMPOSITION

(71) Applicant: NISSAN CHEMICAL CORPORATION, Tokyo (JP)

(72) Inventors: Hiroto Ogata, Toyama (JP); Hirokazu Nishimaki, Toyama (JP); Makoto Nakajima, Toyama (JP); Yuki Mitsutake, Toyama (JP); Hayato Hattori, Toyama (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 335 days.

(21) Appl. No.: 17/625,176

(22) PCT Filed: Jul. 20, 2020

(86) PCT No.: PCT/JP2020/028180
§ 371 (c)(1),
(2) Date: Jan. 6, 2022

(87) PCT Pub. No.: WO2021/015181
PCT Pub. Date: Jan. 28, 2021

(65) Prior Publication Data
US 2022/0283501 A1    Sep. 8, 2022

(30) Foreign Application Priority Data

Jul. 25, 2019 (JP) ................. 2019-136675

(51) Int. Cl.
| | |
|---|---|
| *G03F 7/11* | (2006.01) |
| *C07D 207/404* | (2006.01) |
| *C08G 61/02* | (2006.01) |
| *C08G 61/12* | (2006.01) |
| *C08G 79/04* | (2006.01) |
| *G03F 7/26* | (2006.01) |
| *H01L 21/027* | (2006.01) |
| *H01L 21/033* | (2006.01) |
| *H01L 21/308* | (2006.01) |
| *H01L 21/311* | (2006.01) |

(52) U.S. Cl.
CPC ............ *G03F 7/11* (2013.01); *C07D 207/404* (2013.01); *C08G 61/02* (2013.01); *C08G 61/12* (2013.01); *C08G 79/04* (2013.01); *G03F 7/26* (2013.01); *H01L 21/0275* (2013.01); *H01L 21/0332* (2013.01); *H01L 21/3081* (2013.01); *H01L 21/3086* (2013.01); *H01L 21/31138* (2013.01); *H01L 21/31144* (2013.01); *C08G 2261/12* (2013.01); *C08G 2261/1412* (2013.01); *C08G 2261/1422* (2013.01); *C08G 2261/143* (2013.01); *C08G 2261/312* (2013.01); *C08G 2261/3241* (2013.01); *C08G 2261/3327* (2013.01); *C08L 2203/20* (2013.01)

(58) Field of Classification Search
None
See application file for complete search history.

(56) References Cited

U.S. PATENT DOCUMENTS

| | | | |
|---|---|---|---|
| 2004/0241577 A1 | 12/2004 | Hatakeyama et al. | |
| 2018/0059547 A1 | 3/2018 | Cutler et al. | |
| 2019/0146343 A1* | 5/2019 | Cutler ................. | C08F 230/085 430/323 |
| 2019/0354018 A1* | 11/2019 | Tokunaga .......... | C08G 73/1078 |

FOREIGN PATENT DOCUMENTS

| | | |
|---|---|---|
| JP | 2001-316408 A | 11/2001 |
| JP | 2004-354554 A | 12/2004 |
| JP | 2018-036646 A | 3/2018 |
| JP | 2019-090010 A | 6/2019 |

(Continued)

OTHER PUBLICATIONS

G.-Q. Chen et al., "Synthesis of alternating copolymers of N-substituted maleimides with styrene via atom transfer radical polymerization", Macromolecules, vol. 33, pp. 232-234. (Year: 2000).*
S.K. Meena et al., Thermal study and characterization of new synthesis N-benzylmaleimide and N-phenyl maleimide polymers, International Journal of Engineering Research & Technology, vol. 8, pp. 660-666. (Year: 2019).*
S. Srichan et al., "On the synthesis of sequence-controlled poly(vinyl benzyl amine-co-N-substituted maleimides) copolymers", European Polymer Journal, vol. 62, pp. 338-346. (Year: 2015).*
M. Nakamura et al., "Synthesis and Fluorescent Properties of Conjugated Copolymers Containing Maleimide and Fluorene Units at the Main Chain", Journal of Polymer Science, Part A: Polymer Chemistry, vol. 51, pp. 4945-4956. (Year: 2013).*

(Continued)

*Primary Examiner* — Jiong-Ping Lu
(74) *Attorney, Agent, or Firm* — Oliff PLC

(57) ABSTRACT

A resist underlayer film forming composition contains a reaction product of an aromatic compound (A) having 6 to 60 carbon atoms and a compound represented by formula (B), and a solvent. (In the formula, X represent an oxygen atom or a nitrogen atom; Y represents a single bond, an oxygen atom or a nitrogen atom; X and Y may combine with each other to form a ring; and each of $R_1$, $R_2$, $R_3$ and $R_4$ independently represents a hydrogen atom, an alkyl group having 1 to 20 carbon atoms, a cyclic alkyl group having 3 to 8 carbon atoms or an aromatic group having 6 to 10 carbon atoms; provided that $R_2$ is present only in cases where X is a nitrogen atom, and $R_4$ is present only in cases where Y is a nitrogen atom.)

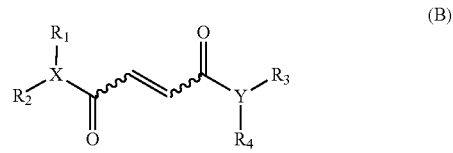

9 Claims, No Drawings

(56) References Cited

FOREIGN PATENT DOCUMENTS

TW            201841961 A     12/2018
WO      WO2018131562      *    7/2018   ............... G03F 7/26

OTHER PUBLICATIONS

Jan. 25, 2022 International Preliminary Report on Patentability issued in International Patent Application No. PCT/JP2020/028180.
Sep. 6, 2023 Office Action issued in Taiwanese Patent Application No. 109124685.
Oct. 13, 2020 International Search Report issued in International Patent Application No. PCT/JP2020/028180.

* cited by examiner

RESIST UNDERLAYER FILM-FORMING COMPOSITION

TECHNICAL FIELD

The present invention relates to a resist underlayer film-forming composition that has a high etching resistance and good optical constants, offers a useful dry etching rate ratio, and exhibits a high coatability even for a so-called stepped substrate and can bury the difference in level to form a flat film having a small variation in film thickness. The present invention also relates to a polymer suitably used in such a resist underlayer film-forming composition, to a resist underlayer film formed using the resist underlayer film-forming composition, and to a method for manufacturing a semiconductor device using the resist underlayer film-forming composition.

BACKGROUND ART

In recent years, resist underlayer film materials for multilayer resist processes are required to function as antireflection films particularly in short-wavelength exposure, to have an appropriate optical constant, and also to exhibit etching resistance during the processing of substrates. The use of polymers that have repeating units containing a benzene ring has been proposed (Patent Literature 1).

CITATION LIST

Patent Literature

Patent Literature 1: JP 2004-354554 A

SUMMARY OF INVENTION

Technical Problem

To cope with the need for thinner resist layers stemming from the miniaturization of resist patterns, a lithography process, in which at least two resist underlayer films are formed and the resist underlayer films are used as mask materials, has been known. In this process, at least one organic film (organic underlayer film) and at least one inorganic underlayer film are formed on a semiconductor substrate. The inorganic underlayer film is patterned while using as a mask a resist pattern formed in an upper resist film, and the resultant pattern is used as a mask in the patterning of the organic underlayer film. The pattern formed in this manner attains a high aspect ratio. For example, the materials for forming the at least two layers are a combination of an organic resin (for example, an acrylic resin or a novolac resin) and an inorganic material (such as a silicon resin (for example, organopolysiloxane) or an inorganic silicon compound (for example, SiON or SiO$_2$)). In recent years, a double patterning technique, in which a single pattern is obtained through two times of lithography and two times of etching while using the multilayer process mentioned above in each of the steps, has widely been used. Here, the organic film formed after the first patterning is required to have a capability of planarizing the difference in level.

Unfortunately, the coatability of resist underlayer film-forming compositions is poor for the so-called stepped substrates that have unevenness due to the difference in height or density of a resist pattern disposed on the workpiece substrate. When a resist underlayer film-forming composition is applied to bury the difference in level, the resultant film has a large variation in film thickness, and there is a problem that the film tends not to be flat.

The present invention has been made based on these problems that are to be solved. An object of the present invention is therefore to provide a resist underlayer film-forming composition that has a high etching resistance and good optical constants, offers a useful dry etching rate ratio, and exhibits a good coatability even for the so-called stepped substrate and can bury the difference in level to form a flat film having a small variation in film thickness. Other objects of the present invention are to provide a polymer suitably used in the resist underlayer film-forming composition, to provide a resist underlayer film formed using the resist underlayer film-forming composition, and to provide a method for manufacturing a semiconductor device using the resist underlayer film-forming composition.

Solution to Problem

The present invention embraces the following.

[1] A resist underlayer film-forming composition comprising a solvent and a reaction product of a C6-C60 aromatic compound (A) with a compound represented by the following formula (B):

[Chemical Formula 1]

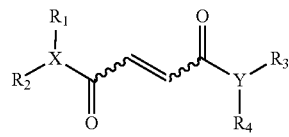

(B)

wherein X denotes an oxygen atom or a nitrogen atom,

Y denotes a single bond, an oxygen atom or a nitrogen atom,

X and Y are optionally bonded to each other to form a ring, $R_1$, $R_2$, $R_3$ and $R_4$ each independently denote a hydrogen atom, a C1-C20 alkyl group, a C3-C8 cycloalkyl group or a C6-C10 aromatic group, $R_2$ is present only when X is a nitrogen atom, and $R_4$ is present only when Y is a nitrogen atom.

[2] The resist underlayer film-forming composition according to [1], wherein X and Y in formula (B) are each an oxygen atom or a nitrogen atom.

[3] The resist underlayer film-forming composition according to [1] or [2], wherein the compound represented by formula (B) is a maleimide derivative represented by the following formula (C):

[Chemical Formula 2]

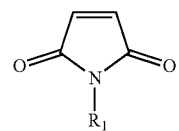

(C)

wherein $R_1$ denotes a hydrogen atom, a C1-C20 alkyl group, a C3-C8 cycloalkyl group or a C6-C10 aromatic group.

[4] The resist underlayer film-forming composition according to [1], wherein the aromatic compound (A) contains one or more benzene rings, one or more naphthalene rings, one or more anthracene rings, one or more pyrene rings, or a combination thereof.

[5] The resist underlayer film-forming composition according to [1], wherein the aromatic compound (A) contains two or more benzene rings, two or more naphthalene rings, two or more anthracene rings, two or more pyrene rings, or a combination thereof.

[6] The resist underlayer film-forming composition according to any one of [1] to [5], further comprising a crosslinking agent.

[7] The resist underlayer film-forming composition according to any one of [1] to [6], further comprising an acid and/or an acid generator.

[8] The resist underlayer film-forming composition according to [1], wherein the solvent has a boiling point of 160° C. or higher.

[9] A resist underlayer film, which is a baked product of a coating film comprising the resist underlayer film-forming composition according to any one of [1] to [8].

[10] A method for manufacturing a semiconductor device, comprising the steps of:

forming on a semiconductor substrate a resist underlayer film using the resist underlayer film-forming composition according to any one of [1] to [8];

forming a resist film on the resist underlayer film;

forming a resist pattern by irradiating the resist film with light or electron beam followed by development;

forming a patterned resist underlayer film by etching the resist underlayer film through the resist pattern formed above; and processing the semiconductor substrate through the patterned resist underlayer film.

[11] A copolymer of a C6-C60 aromatic compound (A) and a maleimide derivative represented by the following formula (C):

[Chemical Formula 3]

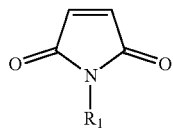

(C)

wherein $R_1$ denotes a hydrogen atom, a C1-C20 alkyl group, a C3-C8 cycloalkyl group or a C6-C10 aromatic group.

[12] The polymer according to [11], wherein the aromatic compound (A) comprises one or more benzene rings, one or more naphthalene rings, one or more anthracene rings or one or more pyrene rings, or a combination thereof.

Advantageous Effects of Invention

The resist underlayer film-forming composition of the present invention not only has a high etching resistance and good optical constants, and offers a useful dry etching rate ratio, but also exhibits a high coatability even for the so-called stepped substrate and can bury the difference in level to form a flat resist underlayer film having a small variation in film thickness, thus allowing for finer substrate processing.

In particular, the resist underlayer film-forming composition of the present invention is effective in a lithography process directed to reducing the resist film thickness, in which at least two resist underlayer films are formed and the resist underlayer films are used as etching masks.

DESCRIPTION OF EMBODIMENTS

Resist Underlayer Film-Forming Composition

A resist underlayer film-forming composition according to the present invention includes a reaction product of a C6-C60 aromatic compound (A) with a compound represented by formula (B) below, a solvent and other components.

[Chemical Formula 4]

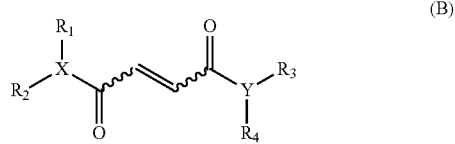

(B)

In the formula, X denotes an oxygen atom or a nitrogen atom,

Y denotes a single bond, an oxygen atom or a nitrogen atom,

X and Y are optionally bonded to each other to form a ring, $R_1$, $R_2$, $R_3$ and $R_4$ each independently denote a hydrogen atom, a C1-C20 alkyl group, a C3-C8 cycloalkyl group or a C6-C10 aromatic group, $R_2$ is present only when X is a nitrogen atom, and $R_4$ is present only when Y is a nitrogen atom. These components will be sequentially described below.

C6-C60 Aromatic Compounds (A)

The C6-C60 aromatic compound (A) may be:
(a) a monocyclic compound such as benzene, phenol or phloroglucinol,
(b) a fused ring compound such as naphthalene or dihydroxynaphthalene,
(c) a heterocyclic compound such as furan, thiophene, pyridine or carbazole,
(d) a compound, in which aromatic rings of the compounds (a) to (c) are bonded via a single bond, such as biphenyl, phenylindole, 9,9-bis(4-hydroxyphenyl) fluorene or α, α, α', α'-tetrakis(4-hydroxyphenyl)-p-xylene, or
(e) a compound, in which aromatic rings of the compounds (a) to (d) are connected via a spacer represented by, for example, —(CH$_2$)$_n$-(n=1 to 20), —CH═CH—, —C═C—, —N═N—, —NH—, —NR—, —NHCO—, —NRCO—, —S—, —COO—, —O—, —CO— or —CH═N—, such as phenylnaphthylamine.

Examples of the aromatic compounds include benzene, thiophene, furan, pyridine, pyrimidine, pyrazine, pyrrole, oxazole, thiazole, imidazole, naphthalene, anthracene, quinoline, carbazole, quinazoline, purine, indolizine, benzothiophene, benzofuran, indole, phenylindole and acridine.

The aromatic compound (A) may be an aromatic compound containing an amino group or a hydroxy group, or both. The aromatic compound (A) may be an arylamine compound or a phenol compound, or a combination of both.

Preferably, the aromatic compound (A) is an aromatic amine or a phenolic hydroxy group-containing compound.

Examples of the aromatic amines include aniline, diphenylamine, phenylnaphthylamine, hydroxydiphenylamine, phenylnaphthylamine, N,N'-diphenylethylenediamine and N,N'-diphenyl-1,4-phenylenediamine.

Examples of the phenolic hydroxy group-containing compounds include phenol, dihydroxybenzene, trihydroxybenzene, hydroxynaphthalene, dihydroxynaphthalene, trihydroxynaphthalene, tris(4-hydroxyphenyl) methane, tris(4-hydroxyphenyl) ethane, 1,1,2,2-tetrakis(4-hydroxyphenyl) ethane and polynuclear phenols.

Examples of the polynuclear phenols include dihydroxybenzene, trihydroxybenzene, hydroxynaphthalene, dihydroxynaphthalene, trihydroxynaphthalene, tris(4-hydroxyphenyl) methane, tris(4-hydroxyphenyl)ethane, 2,2'-biphenol and 1,1,2,2-tetrakis(4-hydroxyphenyl)ethane.

Hydrogen atom in the C6-C60 aromatic compounds (A) may be substituted by C1-C20 alkyl group, fused ring group, heterocyclic group, hydroxy group, amino group, nitro group, ether group, alkoxy group, cyano group and carboxyl group.

Examples of the C1-C20 alkyl groups include optionally substituted, linear or branched alkyl groups such as, for example, methyl group, ethyl group, n-propyl group, isopropyl group, n-butyl group, sec-butyl group, tert-butyl group, n-pentyl group, isopentyl group, neopentyl group, n-hexyl group, isohexyl group, n-heptyl group, n-octyl group, cyclohexyl group, 2-ethylhexyl group, n-nonyl group, isononyl group, p-tert-butylcyclohexyl group, n-decyl group, n-dodecylnonyl group, undecyl group, dodecyl group, tridecyl group, tetradecyl group, pentadecyl group, hexadecyl group, heptadecyl group, octadecyl group, nonadecyl group and eicosyl group. C1-C12 alkyl groups are preferable, C1-C8 alkyl groups are more preferable, and C1-C4 alkyl groups are still more preferable.

The C1-C20 alkyl group, which may be interrupted with an oxygen atom, a sulfur atom or an amide bond, includes the one containing a structural unit represented by —CH$_2$—O—, —CH$_2$—S—, —CH$_2$—NHCO— or —CH$_2$—CONH—, for example. The alkyl group may contain one unit or two or more units of —O—, —S—, —NHCO— or —CONH—. Specific examples of the C1-C20 alkyl group interrupted with an —O—, —S—, —NHCO— or —CONH— unit includes a methoxy group, an ethoxy group, a propoxy group, a butoxy group, a methylthio group, an ethylthio group, a propylthio group, a butylthio group, a methylcarbonylamino group, an ethylcarbonylamino group, a propylcarbonylamino group, a butylcarbonylamino group, a methylaminocarbonyl group, an ethylaminocarbonyl group, a propylaminocarbonyl group and a butylaminocarbonyl group, and further includes a methyl group, an ethyl group, a propyl group, a butyl group, a pentyl group, a hexyl group, a heptyl group, an octyl group, a nonyl group, a decyl group, a dodecyl group and an octadecyl group, each of which is substituted with a substituent such as a methoxy group, an ethoxy group, a propoxy group, a butoxy group, a methylthio group, an ethylthio group, a propylthio group, a butylthio group, a methylcarbonylamino group, an ethylcarbonylamino group, a methylaminocarbonyl group or an ethylaminocarbonyl group. A methoxy group, an ethoxy group, a methylthio group and an ethylthio group are preferable, and a methoxy group and an ethoxy group are more preferable.

The fused ring group is a substituent derived from a fused ring compound. Specific examples thereof include a phenyl group, a naphthyl group, an anthracenyl group, a phenanthrenyl group, a naphthacenyl group, a triphenylenyl group, a pyrenyl group and a chrysenyl group. Of these, a phenyl group, a naphthyl group, an anthracenyl group and a pyrenyl group are preferable.

The heterocyclic group is a substituent derived from a heterocyclic compound. Specific examples thereof include a thiophene group, a furan group, a pyridine group, a pyrimidine group, a pyrazine group, a pyrrole group, an oxazole group, a thiazole group, an imidazole group, a quinoline group, a carbazole group, a quinazoline group, a purine group, an indolizine group, a benzothiophene group, a benzofuran group, an indole group, an acridine group, an isoindole group, a benzimidazole group, an isoquinoline group, a quinoxaline group, a cinnoline group, a pteridine group, a chromene group (benzopyran group), an isochromene group (benzopyran group), a xanthene group, a thiazole group, a pyrazole group, an imidazoline group and anazine group. Of these, a thiophene group, a furan group, a pyridine group, a pyrimidine group, a pyrazine group, a pyrrole group, an oxazole group, a thiazole group, an imidazole group, a quinoline group, a carbazole group, a quinazoline group, a purine group, an indolizine group, a benzothiophene group, a benzofuran group, an indole group and an acridine group are preferable. A thiophene group, a furan group, a pyridine group, a pyrimidine group, a pyrrole group, an oxazole group, a thiazole group, an imidazole group and a carbazole group are most preferable.

The molecule of the aromatic compound mentioned above may be linked together by a single bond or a spacer.

Examples of the spacers include —(CH$_2$)$_n$— (n=1 to 20), —CH<, —CH=CH—, —C≡C—, —N=N—, —NH—, —NR—, —NHCO—, —NRCO—, —S—, —COO—, —O—, —CO—, —CH=N—, and combinations of two or more of these spacers. Two or more of these spacers may be connected.

The aromatic compound (A) preferably contains one or more benzene rings, one or more naphthalene rings, one or more anthracene rings, one or more pyrene rings, or a combination thereof, and more preferably it contains two or more benzene rings, two or more naphthalene rings, two or more anthracene rings, two or more pyrene rings, or a combination thereof.

Some particularly preferred aromatic compounds (A) are illustrated below:

[Chemical Formula 5]

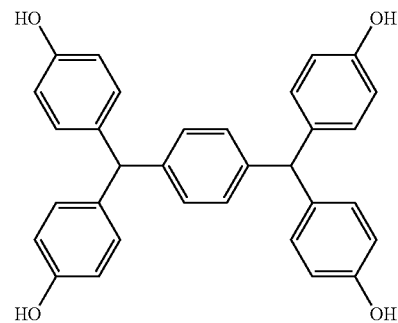

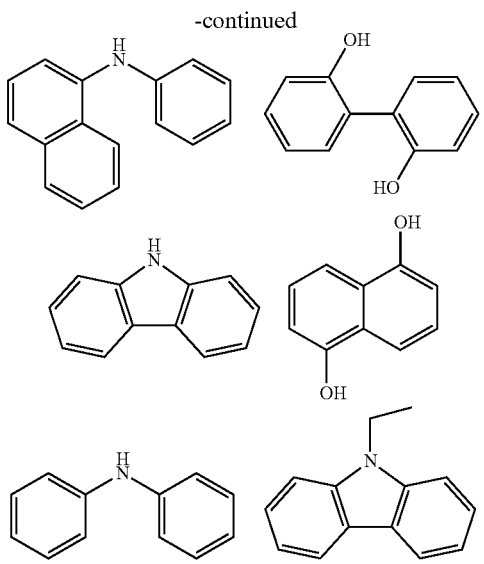

The aromatic compound (A) may be used each alone or in combination of two or more. One or two aromatic compounds (A) are preferably used.

Compound Represented by Formula (B)

The compound (B) is represented by the following formula:

[Chemical Formula 6]

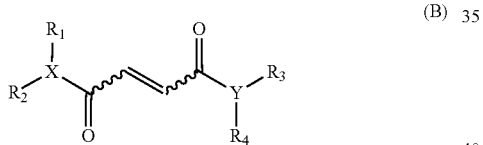

(B)

In the formula, X denotes an oxygen atom or a nitrogen atom,

Y denotes a single bond, an oxygen atom or a nitrogen atom,

X and Y are optionally bonded to each other to form a ring, $R_1$, $R_2$, $R_3$ and $R_4$ each independently denote a hydrogen atom, a C1-C20 alkyl group, a C3-C8 cycloalkyl group or a C6-C10 aromatic group, $R_2$ is present only when X is a nitrogen atom, and $R_4$ is present only when Y is a nitrogen atom.

Examples of the C1-C20 alkyl group include optionally substituted, linear or branched alkyl groups such as, for example, a methyl group, an ethyl group, a n-propyl group, an isopropyl group, a n-butyl group, a sec-butyl group, a tert-butyl group, a n-pentyl group, an isopentyl group, a neopentyl group, a n-hexyl group, an isohexyl group, a n-heptyl group, a n-octyl group, a cyclohexyl group, a 2-ethylhexyl group, a n-nonyl group, an isononyl group, a p-tert-butylcyclohexyl group, a n-decyl group, a n-dodecyl-nonyl group, an undecyl group, a dodecyl group, a tridecyl group, a tetradecyl group, a pentadecyl group, a hexadecyl group, a heptadecyl group, an octadecyl group, a nonadecyl group and an eicosyl group. C1-C12 alkyl groups are preferable, C1-C8 alkyl groups are more preferable, and C1-C4 alkyl groups still more preferable.

Examples of the C3-C8 cycloalkyl group include a cyclopropyl group, a cyclobutyl group, a cyclopentyl group, a cyclohexyl group, a cycloheptyl group and a cyclooctyl group, all of which may be optionally substituted.

Examples of the C6-C10 aromatic group include groups resulting from the removal of one hydrogen atom from an optionally substituted aromatic compound such as benzene, toluene, xylene, mesitylene, cumene, styrene, indene, naphthalene, azulene, anthracene and phenanthrene. A benzyl group and a phenyl group are preferable.

In formula (B), $R_1$ is always present. $R_2$ is present when X is a nitrogen atom but is absent when X is an oxygen atom or when X and Y are bonded to each other to form a ring. $R_3$ is present when Y is an oxygen atom or a nitrogen atom but is absent when Y is a single bond. $R_4$ is present when Y is a nitrogen atom but is absent when Y is an oxygen atom or a single bond or when X and Y are bonded to each other to form a ring.

Preferably, X and Y in formula (B) are each an oxygen atom or a nitrogen atom.

The compound (B) is preferably such that X in formula (B) is a nitrogen atom, Y is a single bond, X and Y are bonded to each other to form a ring, and $R_2$, $R_3$ and $R_4$ are absent.

That is, the compound represented by formula (B) may be a maleimide derivative represented by the following formula (C):

[Chemical Formula 7]

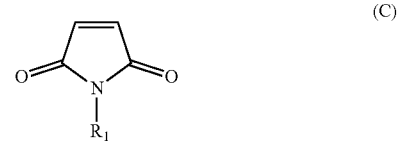

(C)

In the formula, $R_1$ denotes a hydrogen atom, a C1-C20 alkyl group, a C3-C8 cycloalkyl group or a C6-C10 aromatic group.

Here, the C1-C20 alkyl group, the C3-C8 cycloalkyl group and the C6-C10 aromatic group are the same as described hereinabove.

Some particularly preferred compounds (B) are illustrated below:

[Chemical Formula 8]

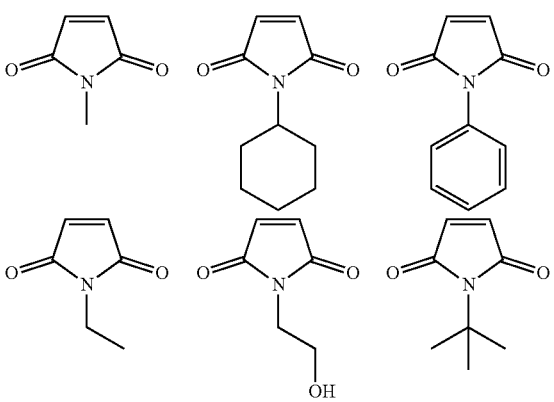

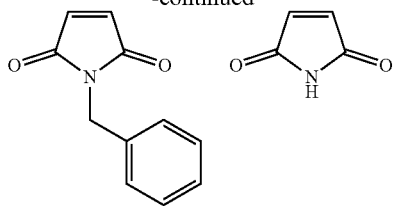

The compound (B) may be used each alone or in combination of two or more. One or two compounds (B) are preferably used.

Reaction Product

Reaction of the aromatic compound (A) with the carbon-carbon double bond in the compound represented by formula (B) may provide a reaction product (a polymer), in which two molecules of the aromatic compound (A) are connected through the two carbon atoms in the compound represented by formula (B). This reaction product is a copolymer of the aromatic compound (A) and the compound represented by formula (B) (preferably, the maleimide derivative represented by formula (C)). As already mentioned, the aromatic compound (A) and the compound represented by formula (B) may be each chosen as a single compound or a combination of two or more compounds, so that the copolymer may be a multicomponent copolymer. Further, a monomer other than the aromatic compound (A) and the compound represented by formula (B) may be copolymerized in an amount not detrimental to the advantageous effects of the present invention (for example, less than 50% by mole, less than 30% by mole, less than 20% by mole, less than 10% by mole or less than 5% by mole).

An acid catalyst is used in the reaction. Examples of the acid catalyst which may be used include mineral acids such as sulfuric acid, phosphoric acid and perchloric acid; organic sulfonic acids such as p-toluenesulfonic acid, p-toluenesulfonic acid monohydrate and methanesulfonic acid; and carboxylic acids such as formic acid and oxalic acid. The amount of acid catalyst used is variable and is selected in accordance with the type of the acid used. The amount is usually within the range of 0.001 to 10000 parts by mass, preferably 0.01 to 1000 parts by mass, and more preferably 0.1 to 100 parts by mass, per 100 parts by mass of the aromatic compound (A).

The above condensation reaction and addition reaction may be carried out without a solvent, but are usually performed using a solvent. Any solvent that does not inhibit the reaction may be used. Examples include ethers such as 1,2-dimethoxyethane, diethylene glycol dimethyl ether, propylene glycol monomethyl ether, propylene glycol monomethyl ether acetate, tetrahydrofuran and dioxane.

Where necessary, a polymerization inhibitor (a radical trapping agent) may be added during the reaction. Specific examples of the polymerization initiator include 2,6-diisobutylphenol, 3,5-di-tert-butylphenol, 3,5-di-tert-butylcresol, hydroquinone, hydroquinone monomethyl ether, pyrogallol, tert-butylcatechol and 4-methoxy-1-naphthol. When a polymerization inhibitor is added, the amount thereof is preferably 1% by mass or less based on the total solid content.

The reaction temperature is usually within the range of 40° C. to 200° C. The reaction time is variable and is selected in accordance with the reaction temperature, but is usually within the range of about 30 minutes to 50 hours.

The weight average molecular weight Mw of the polymer obtained as described above is usually within the range of 500 to 1,000,000, or 600 to 500,000.

Reaction products suitably used in the present invention will be described in Examples.

Solvent

The solvent used in the resist underlayer film-forming composition according to the present invention is not particularly limited as long as the solvent can dissolve the reaction product described above. In particular, in view of the fact that the resist underlayer film-forming composition of the present invention is used as a uniform solution and also in consideration of the applicability of the composition, it is recommended to use a solvent generally used in the lithography process in combination.

Examples of such a solvent include methylcellosolve acetate, ethylcellosolve acetate, propylene glycol, propylene glycol monomethyl ether, propylene glycol monoethyl ether, methyl isobutyl carbinol, propylene glycol monobutyl ether, propylene glycol monomethyl ether acetate, propylene glycol monoethyl ether acetate, propylene glycol monopropyl ether acetate, propylene glycol monobutyl ether acetate, toluene, xylene, methyl ethyl ketone, cyclopentanone, cyclohexanone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl pyruvate, ethyl pyruvate, ethylene glycol monomethyl ether, ethylene glycol monoethyl ether, ethylene glycol monopropyl ether, ethylene glycol monobutyl ether, ethylene glycol monomethyl ether acetate, ethylene glycol monoethyl ether acetate, ethylene glycol monopropyl ether acetate, ethylene glycol monobutyl ether acetate, diethylene glycol dimethyl ether, diethylene glycol diethyl ether, diethylene glycol dipropyl ether, diethylene glycol dibutyl ether, propylene glycol monomethyl ether, propylene glycol dimethyl ether, propylene glycol diethyl ether, propylene glycol dipropyl ether, propylene glycol dibutyl ether, ethyl lactate, propyl lactate, isopropyl lactate, butyl lactate, isobutyl lactate, methyl formate, ethyl formate, propyl formate, isopropyl formate, butyl formate, isobutyl formate, amyl formate, isoamyl formate, methyl acetate, ethyl acetate, amyl acetate, isoamyl acetate, hexyl acetate, methyl propionate, ethyl propionate, propyl propionate, isopropyl propionate, butyl propionate, isobutyl propionate, methyl butyrate, ethyl butyrate, propyl butyrate, isopropyl butyrate, butyl butyrate, isobutyl butyrate, ethyl hydroxyacetate, ethyl 2-hydroxy-2-methylpropionate, methyl 3-methoxy-2-methylpropionate, methyl 2-hydroxy-3-methylbutyrate, ethyl methoxyacetate, ethyl ethoxyacetate, methyl 3-methoxypropionate, ethyl 3-ethoxypropionate, ethyl 3-methoxypropionate, 3-methoxybutyl acetate, 3-methoxypropyl acetate, 3-methyl-3-methoxybutyl acetate, 3-methyl-3-methoxybutyl propionate, 3-methyl-3-methoxybutyl butyrate, methyl acetoacetate, toluene, xylene, methyl ethyl ketone, methyl propyl ketone, methyl butyl ketone, 2-heptanone, 3-heptanone, 4-heptanone, cyclohexanone, N,N-dimethylformamide, N-methylacetamide, N,N-dimethylacetamide, N-methylpyrrolidone, 4-methyl-2-pentanol and γ-butyrolactone. The solvent may be used each alone or in combination of two or more.

Further, the following compounds described in WO 2018/131562 A1 may also be used.

[Chemical Formula 9]

Formula (i)

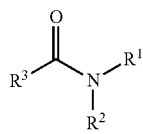

In formula (i), $R^1$, $R^2$ and $R^3$ each denote a hydrogen atom or a C1-C20 alkyl group optionally interrupted with an oxygen atom, a sulfur atom or an amide bond, which are the same as or different from one another, and are optionally bonded together to form a ring structure.

Examples of the C1-C20 alkyl group include optionally substituted, linear or branched alkyl groups such as, for example, a methyl group, an ethyl group, a n-propyl group, an isopropyl group, a n-butyl group, a sec-butyl group, a tert-butyl group, a n-pentyl group, an isopentyl group, a neopentyl group, a n-hexyl group, an isohexyl group, a n-heptyl group, a n-octyl group, a cyclohexyl group, a 2-ethylhexyl group, a n-nonyl group, an isononyl group, a p-tert-butylcyclohexyl group, a n-decyl group, a n-dodecyl-nonyl group, an undecyl group, a dodecyl group, a tridecyl group, a tetradecyl group, a pentadecyl group, a hexadecyl group, a heptadecyl group, an octadecyl group, a nonadecyl group and an eicosyl group. C1-C12 alkyl groups are preferable, C1-C8 alkyl groups are more preferable, and C1-C4 alkyl groups still more preferable.

Examples of the C1-C20 alkyl group interrupted with an oxygen atom, a sulfur atom or an amide bond include the ones containing a structural unit represented by —CH₂—O—, —CH₂—S—, —CH₂—NHCO— or —CH₂—CONH—. The alkyl group may contain one unit or two or more units of —O—, —S—, —NHCO— or —CONH—. Specific examples of the C1-C20 alkyl group interrupted with an —O—, —S—, —NHCO— or —CONH— unit include a methoxy group, an ethoxy group, a propoxy group, a butoxy group, a methylthio group, an ethylthio group, a propylthio group, a butylthio group, a methylcarbonylamino group, an ethylcarbonylamino group, a propylcarbonylamino group, a butylcarbonylamino group, a methylaminocarbonyl group, an ethylaminocarbonyl group, a propylaminocarbonyl group and a butylaminocarbonyl group. They further include a methyl group, an ethyl group, a propyl group, a butyl group, a pentyl group, a hexyl group, a heptyl group, an octyl group, a nonyl group, a decyl group, a dodecyl group and an octadecyl group, each of which is substituted with a substituent such as a methoxy group, an ethoxy group, a propoxy group, a butoxy group, a methylthio group, an ethylthio group, a propylthio group, a butylthio group, a methylcarbonylamino group, an ethylcarbonylamino group, a methylaminocarbonyl group or an ethylaminocarbonyl group. A methoxy group, an ethoxy group, a methylthio group and an ethylthio group are preferable, and a methoxy group and an ethoxy group are more preferable.

The solvent mentioned above have a relatively high boiling point and are therefore effective for imparting high gap-filling properties and high flattening properties to the resist underlayer film-forming composition.

Specific examples of preferred compound represented by formula (i) are illustrated below:

[Chemical Formula 10]

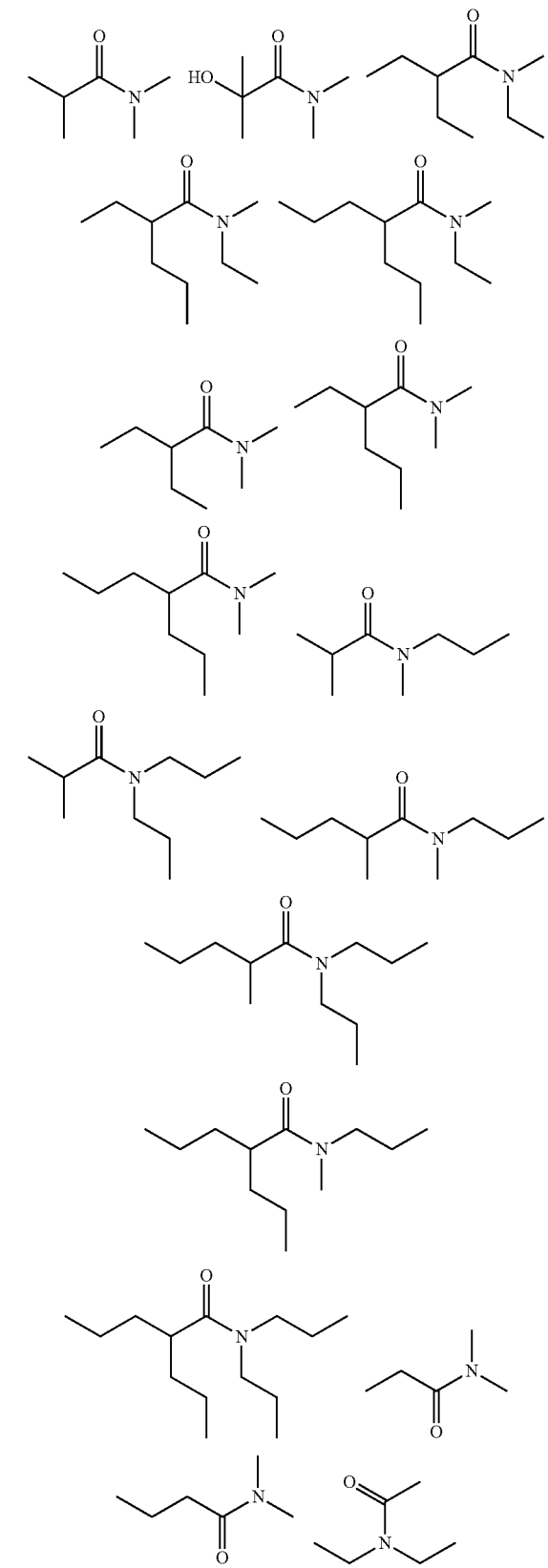

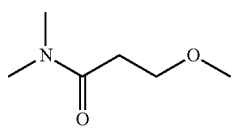

Of the compounds illustrated above, 3-methoxy-N,N-dimethylpropionamide, N,N-dimethylisobutyramide, and the compounds represented by the following formulas are preferable.

[Chemical Formula 11]

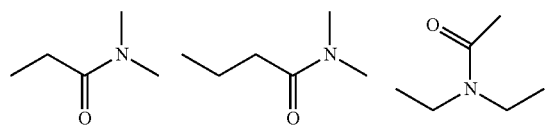

Particularly preferred compounds represented by formula (i) are 3-methoxy-N,N-dimethylpropionamide and N,N-dimethylisobutyramide.

The solvent mentioned above may be used each alone or in combination of two or more. Of these solvents, those having a boiling point of 160° C. or higher are preferable. Some preferred solvents are propylene glycol monomethyl ether, propylene glycol monomethyl ether acetate, ethyl lactate, butyl lactate, cyclohexanone, 3-methoxy-N,N-dimethylpropionamide, N,N-dimethylisobutyramide, 2,5-dimethylhexane-1,6-diyl diacetate (DAH; cas, 89182-68-3) and 1,6-diacetoxyhexane (cas, 6222-17-9). Propylene glycol monomethyl ether, propylene glycol monomethyl ether acetate and N,N-dimethylisobutyramide are particularly preferable.

Crosslinking Agent Component

The resist underlayer film-forming composition of the present invention may include a crosslinking agent component. Examples of the crosslinking agent include melamine compounds, substituted urea compounds, and polymers thereof. Those crosslinking agents having at least two crosslinking substituents are preferable, with examples including methoxymethylated glycoluril (for example, tetramethoxymethyl glycoluril), butoxymethylated glycoluril, methoxymethylated melamine, butoxymethylated melamine, methoxymethylated benzoguanamine, butoxymethylated benzoguanamine, methoxymethylated urea, butoxymethylated urea and methoxymethylated thiourea. Further, condensates of these compounds may also be used.

The crosslinking agent used may be a crosslinking agent having a high heat resistance. The crosslinking agent having a high heat resistance may be suitably a compound that contains, in the molecule, a crosslinking substituent having an aromatic ring (for example, a benzene ring or a naphthalene ring).

Examples of such compounds include compounds having a partial structure of the following formula (4), and polymers or oligomers having a repeating unit of the following formula (5):

[Chemical Formula 12]

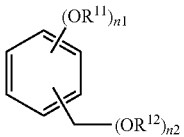
Formula (4)

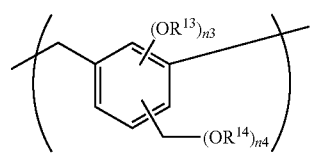
Formula (5)

$R^{11}$, $R^{12}$, $R^{13}$ and $R^{14}$ are each a hydrogen atom or a C1-C10 alkyl group. Examples of the alkyl group are as disclosed above.

Examples of the compound of formula (4) and the polymer and oligomer of formula (5) include the following:

[Chemical Formula 13]

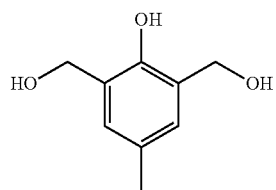
Formula (4-1)

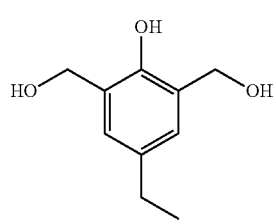
Formula (4-2)

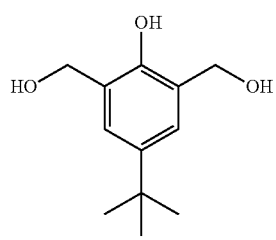
Formula (4-3)

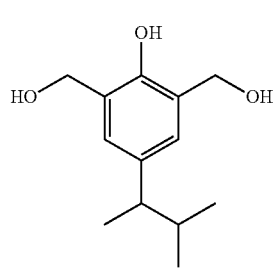
Formula (4-4)

Formula (4-5)
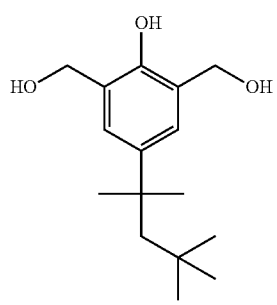
Formula (4-6)
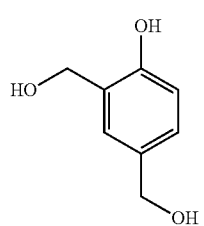
Formula (4-7)
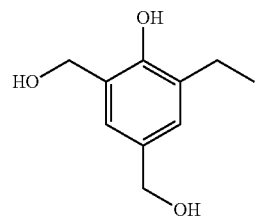
Formula (4-8)
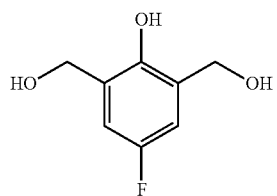
Formula (4-9)
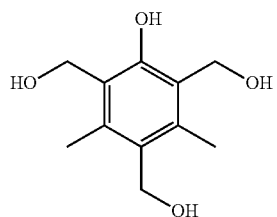
Formula (4-10)
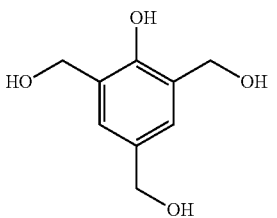
Formula (4-11)
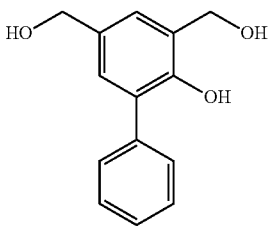
Formula (4-12)
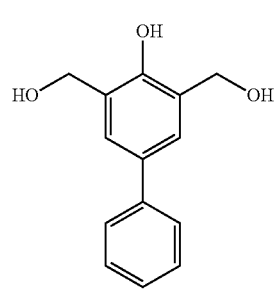
Formula (4-13)
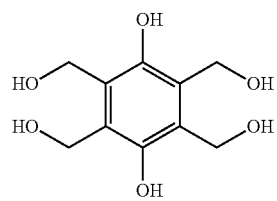
Formula (4-14)
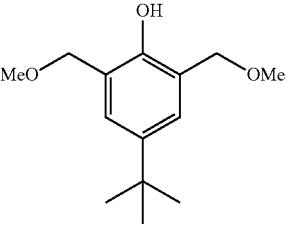
Formula (4-15)
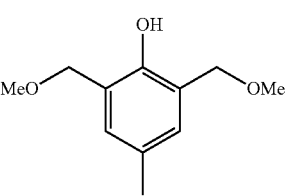
[Chemical Formula 14]
Formula (4-16)
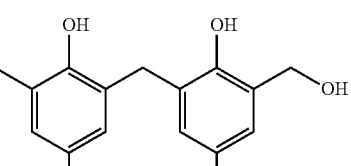
Formula (4-17)
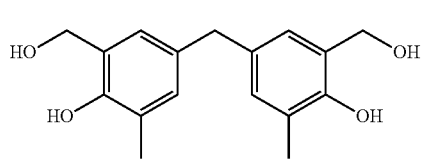
Formula (4-18)
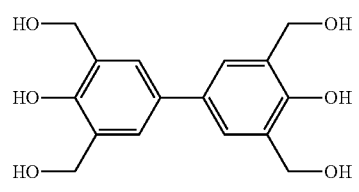

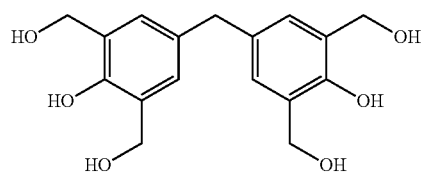
Formula (4-19)

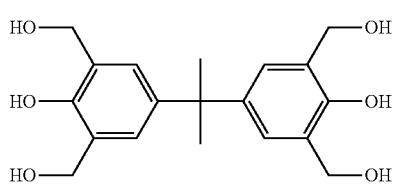
Formula (4-20)

Formula (4-21)
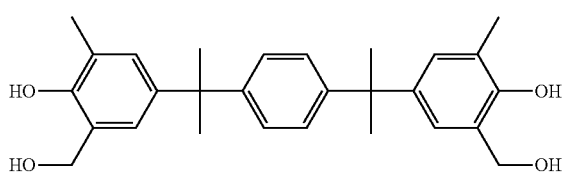

Formula (4-22)
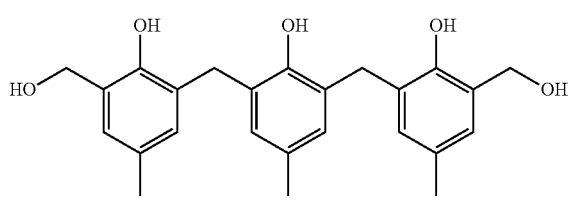

Formula (4-23)
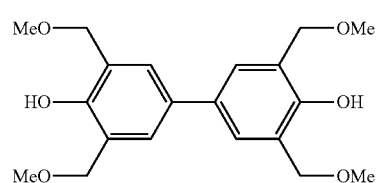

Formula (4-24)
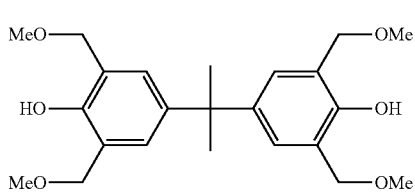

Formula (4-25)
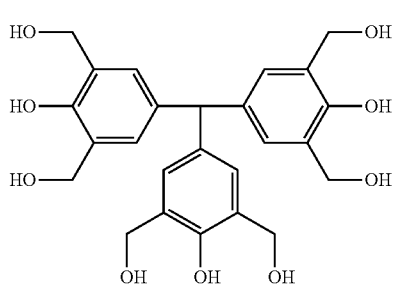

Formula (4-26)
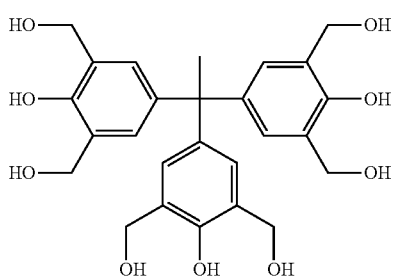

Formula (4-27)
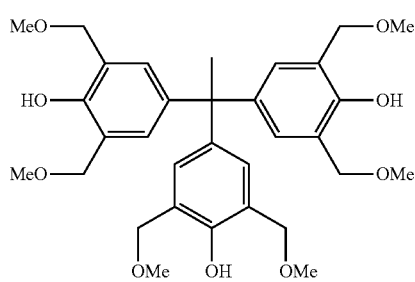

The compounds described above may be obtained as products of ASAHI YUKIZAI CORPORATION and Honshu Chemical Industry Co., Ltd. Among the crosslinking agents illustrated above, for example, the compound of formula (4-24) is available under the product name TM-BIP-A from ASAHI YUKIZAI CORPORATION.

The amount of the crosslinking agent added varies depending on such factors as the coating solvent used, the base substrate used, the required solution viscosity and the required film shape, but it may be within the range of 0.001 to 80% by mass, preferably 0.01 to 50% by mass, and more preferably 0.05 to 40% by mass, based on the total solid content. The crosslinking agents described above may undergo a crosslinking reaction by self-condensation, but they may cause a crosslinking reaction with a crosslinking substituent of the reaction product of the present invention, when the reaction product contains the crosslinking substituent.

Acid and/or Acid Generator

The resist underlayer film-forming composition of the present invention may contain an acid and/or an acid generator.

Examples of the acid include p-toluenesulfonic acid, trifluoromethanesulfonic acid, pyridinium p-toluenesulfonic acid, pyridinium phenolsulfonic acid, salicylic acid, 5-sulfosalicylic acid, 4-phenolsulfonic acid, camphorsulfonic acid, 4-chlorobenzenesulfonic acid, benzenedisulfonic acid, 1-naphthalenesulfonic acid, citric acid, benzoic acid, hydroxybenzoic acid and naphthalenecarboxylic acid.

The acid may be used each alone or in combination of two or more. The amount is usually within the range of 0.0001 to 20% by mass, preferably 0.0005 to 10% by mass, and more preferably 0.01 to 3% by mass, based on the total solid content.

Examples of the acid generator include thermal acid generators and photo acid generators.

Examples of the thermal acid generators include 2,4,4,6-tetrabromocyclohexadienone, benzoin tosylate, 2-nitrobenzyl tosylate, K-PURE (registered trademark) series CXC-1612, CXC-1614, TAG-2172, TAG-2179, TAG-2678, TAG 2689 and TAG 2700 (manufactured by King Industries), SI-45, SI-60, SI-80, SI-100, SI-110 and SI-150 (manufactured by SANSHIN CHEMICAL INDUSTRY CO., LTD.), and other organosulfonic acid alkyl esters.

Photo acid generators generate an acid, when the resist is exposed to light, whereby the acidity of underlayer film can be adjusted. The use of a photo acid generator is an approach to adjust the acidity of the underlayer film to that of the resist layer to be formed thereon. Further, the shape of a pattern formed in the upper resist layer may be controlled by adjusting the acidity of the underlayer film.

Examples of the photo acid generator contained in the resist underlayer film-forming composition of the present invention include onium salt compounds, sulfonimide compounds and disulfonyl diazomethane compounds.

Examples of the onium salt compounds include iodonium salt compounds such as diphenyliodonium hexafluorophosphate, diphenyliodonium trifluoromethanesulfonate, diphenyliodonium nonafluoro-normal butane sulfonate, diphenyliodonium perfluoro-normal octane sulfonate, diphenyliodonium camphorsulfonate, bis(4-tert-butylphenyl)iodonium camphorsulfonate and bis(4-tert-butylphenyl)iodonium trifluoromethanesulfonate, and sulfonium salt compounds such as triphenylsulfonium hexafluoroantimonate, triphenylsulfonium nonafluoro-normal butane sulfonate, triphenylsulfonium camphorsulfonate and triphenylsulfonium trifluoromethanesulfonate.

Examples of the sulfonimide compounds include N-(trifluoromethanesulfonyloxy)succinimide, N-(nonafluoro-normal butane sulfonyloxy)succinimide, N-(camphorsulfonyloxy)succinimide and N-(trifluoromethanesulfonyloxy)naphthalimide.

Examples of the disulfonyl diazomethane compounds include bis(trifluoromethylsulfonyl)diazomethane, bis(cyclohexylsulfonyl)diazomethane, bis(phenylsulfonyl)diazomethane, bis(p-toluenesulfonyl)diazomethane, bis(2,4-dimethylbenzenesulfonyl)diazomethane and methyl sulfonyl-p-toluenesulfonyldiazomethane.

The acid generator may be used each alone or in combination of two or more.

When an acid generator is used, the ratio thereof is within the range of 0.01 to 5 parts by mass, 0.1 to 3 parts by mass, or 0.5 to 1 part by mass, per 100 parts by mass of the solid content in the resist underlayer film-forming composition.

Other Components

To reduce the occurrence of defects such as pinholes or striation and to further enhance the applicability to surface unevenness, the resist underlayer film-forming composition of the present invention may further include a surfactant. Examples of the surfactant include nonionic surfactants such as polyoxyethylene alkyl ethers including polyoxyethylene lauryl ether, polyoxyethylene stearyl ether, polyoxyethylene cetyl ether and polyoxyethylene oleyl ether, polyoxyethylene alkylaryl ethers including polyoxyethylene octylphenol ether and polyoxyethylene nonylphenol ether, polyoxyethylene/polyoxypropylene block copolymers, sorbitan fatty acid esters including sorbitan monolaurate, sorbitan monopalmitate, sorbitan monostearate, sorbitan monooleate, sorbitan trioleate and sorbitan tristearate, and polyoxyethylene sorbitan fatty acid esters including polyoxyethylene sorbitan monolaurate, polyoxyethylene sorbitan monopalmitate, polyoxyethylene sorbitan monostearate, polyoxyethylene sorbitan trioleate and polyoxyethylene sorbitan tristearate, fluorosurfactants such as EFTOP series EF301, EF303 and EF352 (produce names, manufactured by Mitsubishi Materials Electronic Chemicals Co., Ltd.), MEGAFACE series F171, F173, R-40, R-40N and R-40LM (produce names, manufactured by DIC CORPORATION), Fluorad series FC430 and FC431 (produce names, manufactured by Sumitomo 3M Limited), AsahiGuard AG710, and Surflon series S-382, SC101, SC102, SC103, SC104, SC105 and SC106 (produce names, manufactured by AGC Inc.), and organosiloxane polymer KP341 (manufactured by Shin-Etsu Chemical Co., Ltd.). The amount of the surfactant added is usually 2.0% by mass or less, and preferably 1.0% by mass or less, based on the total solid content of the resist underlayer film materials. The surfactant may be used each alone or in combination of two or more. When a surfactant is used, the ratio thereof is within the range of 0.0001 to 5 parts by mass, 0.001 to 1 part by mass, or 0.01 to 0.5 parts by mass, per 100 parts by mass of the solid content in the resist underlayer film-forming composition.

Other components such as light absorbers, rheology modifiers and adhesion aids may be added to the resist underlayer film-forming composition of the present invention. Rheology modifiers are effective for enhancing the fluidity of the underlayer film-forming composition. Adhesion aids are effective for enhancing the adhesion between a semiconductor substrate or a resist and an underlayer film.

Some example light absorbers, which may be suitably used, are commercially available light absorbers described in "Kougyouyou Shikiso no Gijutsu to Shijou (Technology and Market of Industrial Dyes)" (CMC Publishing Co., Ltd.) and "Senryou Binran (Dye Handbook)" (edited by The Society of Synthetic Organic Chemistry, Japan), such as, for example, C. I. Disperse Yellow 1, 3, 4, 5, 7, 8, 13, 23, 31, 49, 50, 51, 54, 60, 64, 66, 68, 79, 82, 88, 90, 93, 102, 114 and 124; C. I. Disperse Orange 1, 5, 13, 25, 29, 30, 31, 44, 57, 72 and 73; C. I. Disperse Red 1, 5, 7, 13, 17, 19, 43, 50, 54, 58, 65, 72, 73, 88, 117, 137, 143, 199 and 210; C. I. Disperse Violet 43; C. I. Disperse Blue 96; C. I. Fluorescent Brightening Agent 112, 135 and 163; C. I. Solvent Orange 2 and 45; C. I. Solvent Red 1, 3, 8, 23, 24, 25, 27 and 49; C. I. Pigment Green 10; and C. I. Pigment Brown 2. The light absorber is usually added in a proportion of 10% by mass or less, and preferably 5% by mass or less, based on the total solid content in the resist underlayer film-forming composition.

The rheology modifier may be added mainly to enhance the fluidity of the resist underlayer film-forming composition and thereby, particularly in the baking step, to increase the uniformity in thickness of the resist underlayer film and to enhance the filling performance of the resist underlayer film-forming composition for the inside of holes. Specific examples thereof include phthalic acid derivatives such as dimethyl phthalate, diethyl phthalate, diisobutyl phthalate, dihexyl phthalate and butyl isodecyl phthalate; adipic acid derivatives such as di-n-butyl adipate, diisobutyl adipate, diisooctyl adipate and octyl decyl adipate; maleic acid derivatives such as di-n-butyl maleate, diethyl maleate and dinonyl maleate; oleic acid derivatives such as methyl oleate, butyl oleate and tetrahydrofurfuryl oleate; and stearic acid derivatives such as n-butyl stearate and glyceryl stearate. The rheology modifier is usually added in a proportion of less than 30% by mass relative to the total solid content in the resist underlayer film-forming composition.

The adhesion aid may be added mainly to enhance the adhesion between a substrate or a resist and the resist underlayer film-forming composition and thereby to prevent the detachment of the resist, particularly during the development. Specific examples thereof include chlorosilanes such as trimethylchlorosilane, dimethylmethylolchlorosilane, methyldiphenylchlorosilane and chloromethyldimethylchlorosilane; alkoxysilanes such as trimethylmethoxysilane, dimethyldiethoxysilane, methyldimethoxysilane, dimethylmethylolethoxysilane, diphenyldimethoxysilane and phenyltriethoxysilane; silazanes such as hexamethyldisilazane, N,N-bis(trimethylsilyl)urea, dimethyltrimethylsilylamine and trimethylsilylimidazole; silanes such as methyloltrichlorosilane, γ-chloropropyltrimethoxysilane, γ-aminopropyltriethoxysilane and γ-glycidoxypropyltrimethoxysilane; heterocyclic compounds such as benzotriazole, benzimidazole, indazole, imidazole, 2-mercaptobenzimidazole, 2-mercaptobenzothiazole, 2-mercaptobenzoxazole, urazole, thiouracyl, mercaptoimidazole and mercaptopyrimidine; and urea or thiourea compounds such as 1,1-dimethylurea and 1,3-dimethylurea. The adhesion aid is usually added in a proportion of less than 5% by mass, and preferably less than 2% by mass, relative to the total solid content in the resist underlayer film-forming composition.

The solid content in the resist underlayer film-forming composition according to the present invention is usually within the range of 0.1 to 70% by mass, and preferably 0.1 to 60% by mass. The solid content is the proportion of all the components of the resist underlayer film-forming composition except the solvent. The proportion of the reaction product in the solid content may be 1 to 100% by mass, 1 to 99.9% by mass, 50 to 99.9% by mass, 50 to 95% by mass, or 50 to 90% by mass, with increasing preference.

A measure for evaluating the uniformity of the solution of the resist underlayer film-forming composition is to observe the passing property of the composition through a prescribed microfilter. The resist underlayer film-forming composition of the present invention is capable of passing through a microfilter having a pore diameter of 0.1 μm, and thus it is in a uniform solution state.

Examples of the microfilter material include fluororesins such as PTFE (polytetrafluoroethylene) and PFA (tetrafluoroethylene/perfluoroalkyl vinyl ether copolymer), PE (polyethylene), UPE (ultrahigh molecular weight polyethylene), PP (polypropylene), PSF (polysulfone), PES (polyethersulfone) and nylon, with PTFE (polytetrafluoroethylene) being preferable.

Resist Underlayer Film and Method for Manufacturing Semiconductor Device

Hereinbelow, the resist underlayer film from the resist underlayer film-forming composition of the present invention, and the method for manufacturing a semiconductor device will be described.

The resist underlayer film-forming composition of the present invention is applied with an appropriate technique such as a spinner or a coater onto a semiconductor device substrate (such as, for example, a silicon wafer substrate, a silicon/silicon dioxide coated substrate, a silicon nitride substrate, a glass substrate, an ITO substrate, a polyimide substrate, or a low dielectric constant material (low-k material) coated substrate), and the coating is baked to form a resist underlayer film. The baking conditions are appropriately selected from baking temperatures of 80° C. to 400° C. and amounts of baking time of 0.3 to 60 minutes. The baking temperature is preferably within the range of 150° C. to 350° C., and the baking time is preferably within the range of 0.5 to 2 minutes. Here, the film thickness of the underlayer film formed is, for example, within the range of 10 to 1000 nm, or 20 to 500 nm, or 30 to 400 nm, or 50 to 300 nm.

Further, an inorganic resist underlayer film (a hard mask) may be formed on the organic resist underlayer film according to the present invention. For example, such a hard mask may be formed by spin-coating of a silicon-containing resist underlayer film (inorganic resist underlayer film) forming composition described in WO 2009/104552 A1, or by CVD of a Si-based inorganic material.

The resist underlayer film-forming composition according to the present invention may be applied onto a semiconductor substrate having a stepped region and a stepless region (so-called stepped substrate) and may be baked to form a resist underlayer film having a difference in level in the range of 3 to 70 nm between the stepped region and the stepless region.

Next, a resist film, for example, a photoresist layer is formed on the resist underlayer film. The photoresist layer may be formed by a known method, namely, by applying a photoresist composition solution onto the underlayer film followed by baking. The film thickness of the photoresist is, for example, 50 to 10000 nm, or 100 to 2000 nm, or 200 to 1000 nm.

The photoresist applied onto the resist underlayer film is not particularly limited as long as it is sensitive to light used in the photoexposure. Negative photoresists and positive photoresists may be used. Examples include positive photoresists composed of a novolac resin and a 1,2-naphthoquinonediazide sulfonic acid ester; chemically amplified photoresists composed of a photo acid generator and a binder having a group that is decomposed by an acid to increase the alkali dissolution rate; chemically amplified photoresists composed of an alkali-soluble binder, a photo acid generator, and a low-molecular compound that is decomposed by an acid to increase the alkali dissolution rate of the photoresist; and chemically amplified photoresists composed of a photo acid generator, a binder having a group that is decomposed by an acid to increase the alkali dissolution rate, and a low-molecular compound that is decomposed by an acid to increase the alkali dissolution rate of the photoresist. Specific examples include those available under the produce names of APEX-E from Shipley, PAR 710 from Sumitomo Chemical Co., Ltd., and SEPR 430 from Shin-Etsu Chemical Co., Ltd. Examples further include fluorine-containing polymer-based photoresists described in Proc. SPIE, Vol. 3999, 330-334 (2000), Proc. SPIE, Vol. 3999, 357-364 (2000), and Proc. SPIE, Vol. 3999, 365-374 (2000).

Next, a resist pattern is formed by irradiation with a light or an electron beam and development. Exposure through a predetermined mask is first conducted. In the exposure, for example, a near ultraviolet light, a far ultraviolet light, or an extreme ultraviolet light (for example, an EUV (wavelength: 13.5 nm)) is used. Specifically, for example, a KrF excimer laser (wavelength: 248 nm), an ArF excimer laser (wavelength: 193 nm), or an $F_2$ excimer laser (wavelength: 157 nm) may be used. Of these, an ArF excimer laser (wavelength: 193 nm) and an EUV (wavelength: 13.5 nm) are preferred. After the exposure, if necessary, post exposure bake may be performed. The post exposure bake is performed under conditions appropriately selected from those at a heating temperature of 70 to 150° C. for a heating time of 0.3 to 10 minutes.

Further, in the present invention, as a resist, instead of the photoresist, a resist for electron beam lithography may be used. Any of a negative electron beam resist and a positive electron beam resist may be used. Examples include chemically amplified resists composed of an acid generator and a binder having a group that is decomposed by an acid to give rise to a change in alkali dissolution rate; chemically amplified resists composed of an alkali-soluble binder, an acid generator, and a low-molecular compound that is decomposed by an acid to change the alkali dissolution rate of the resist; chemically amplified resists composed of an acid generator, a binder having a group that is decomposed by an acid to give rise to a change in alkali dissolution rate, and a low-molecular compound that is decomposed by an acid to change the alkali dissolution rate of the resist; non-chemically amplified resists composed of a binder having a group that is decomposed by an electron beam to give rise to a change in alkali dissolution rate, and non-chemically amplified resists composed of a binder having a moiety that is cleaved by an electron beam to give rise to a change in alkali dissolution rate. Also when using the above electron beam resist, a resist pattern may be similarly formed as in the case where a photoresist is used and an electron beam is used as a source of irradiation.

Next, the resist is developed with a developing solution. In the development, for example, when a positive photoresist is used, the exposed portion of the photoresist is removed, so that a photoresist pattern is formed.

Examples of the developing solutions include alkaline aqueous solutions, for example, aqueous solution of alkali metal hydroxide such as potassium hydroxide and sodium hydroxide; aqueous solution of quaternary ammonium hydroxide such as tetramethylammonium hydroxide, tetraethylammonium hydroxide and choline; and aqueous solution of amine such as ethanolamine, propylamine and ethylenediamine. Further, additives such as surfactant may be added to the developing solution. Conditions for the development are appropriately selected from those at a temperature of 5 to 50° C. for a time of 10 to 600 seconds.

Subsequently, using the thus formed photoresist (upper layer) pattern as a protective film, the inorganic underlayer film (intermediate layer) is removed, and then, using a film comprising the patterned photoresist and inorganic underlayer film (intermediate layer) as a protective film, the organic underlayer film (lower layer) is removed. Finally, using the patterned inorganic underlayer film (intermediate layer) and organic underlayer film (lower layer) as a protective film, processing of the semiconductor substrate is performed.

First, a portion of the inorganic underlayer film (intermediate layer), from which the photoresist is removed, is removed by dry etching so that the semiconductor substrate is exposed. The dry etching of the inorganic underlayer film may be performed using a gas such as tetrafluoromethane ($CF_4$), perfluorocyclobutane ($C_4F_8$), perfluoropropane ($C_3F_8$), trifluoromethane, carbon monoxide, argon, oxygen, nitrogen, sulfur hexafluoride, difluoromethane, nitrogen trifluoride, chlorine trifluoride, chlorine, trichloroborane or dichloroborane. A halogen-containing gas is preferably used in the dry etching of the inorganic underlayer film, and a fluorine-containing gas is more preferably used. Examples of the fluorine-containing gases include tetrafluoromethane ($CF_4$), perfluorocyclobutane ($C_4F_8$), perfluoropropane ($C_3F_8$), trifluoromethane and difluoromethane ($CH_2F_2$).

Then, using a film comprising the patterned photoresist and inorganic underlayer film as a protective film, the organic underlayer film is removed. The organic underlayer film (lower layer) is preferably removed by dry etching using an oxygen-based gas. The reason for this is that the inorganic underlayer film containing silicon atoms in a large amount is unlikely to be removed by dry etching using an oxygen-based gas.

Lastly, the semiconductor substrate is processed. The semiconductor substrate is preferably processed by dry etching with a fluorine-containing gas.

Examples of the fluorine-containing gases include tetrafluoromethane ($CF_4$), perfluorocyclobutane ($C_4F_8$), perfluoropropane ($C_3F_8$), trifluoromethane and difluoromethane ($CH_2F_2$).

Before the formation of the photoresist, an organic antireflective film may be formed on the upper layer of the resist underlayer films. The antireflective coating composition used herein is not particularly limited and may be appropriately selected from the compositions conventionally used in the lithographic processes. The antireflective film may be formed by a conventional method, for example, by application with a spinner or a coater followed by baking.

In the present invention, an organic underlayer film may be formed on a substrate, thereafter an inorganic underlayer film may be formed thereon, and further a photoresist may be formed thereon. By virtue of this, even when a substrate is covered with a photoresist having a smaller thickness for preventing an occurrence of pattern collapse due to a reduced pattern width of the photoresist, appropriate selection of an etching gas enables processing of the substrate. For example, the resist underlayer film may be processed using as the etching gas a fluorine-containing gas capable of etching the photoresist at a sufficiently high rate; the substrate may be processed using as the etching gas a fluorine-containing gas capable of etching the inorganic underlayer film at a sufficiently high rate; and further the substrate may be processed using as the etching gas an oxygen-containing gas capable of etching the organic underlayer film at a sufficiently high rate.

The resist underlayer film formed from the resist underlayer film-forming composition sometimes shows an absorption with respect to the light used in the lithographic process, depending on the wavelength of the light. In such a case, the film may function as an antireflective film to effectively prevent the reflection of light from the substrate. Further, the underlayer film formed from the resist underlayer film-forming composition of the present invention may also function as a hard mask. The underlayer film of the present invention may be used as, for example, a layer for preventing the interaction between a substrate and a photoresist, a layer having a function to prevent adverse effects on a substrate by a material used in a photoresist or by a substance generated during the photoexposure of a photoresist, a layer having a function to prevent the diffusion of substances generated from a substrate during heating and baking into an upper photoresist layer, and a barrier layer for reducing the poisoning effects on a photoresist layer by a semiconductor substrate dielectric layer.

Further, the underlayer film formed from the resist underlayer film-forming composition may be used as a gap-filling material that is applied to a substrate with via holes used in the dual damascene process and can fill the holes without clearance. Furthermore, the underlayer film may also be used as a flattening material for flattening the surface of an irregular semiconductor substrate.

EXAMPLES

Specific examples of the resist underlayer film-forming compositions of the present invention will be described hereinbelow with reference to the following Examples. However, it should be construed that the scope of the present invention is not limited thereto.

The equipment such as apparatus used for the measurement of the weight average molecular weight of reaction products obtained in Synthesis Examples are described below.

Apparatus: HLC-8320 GPC manufactured by Tosoh Corporation
GPC columns: TSKgel Super-Multipore HZ-N (two columns)
Column temperature: 40° C.
Flow rate: 0.35 ml/min
Eluent: THF
Standard samples: Polystyrenes (SHOWA DENKO K.K.)

Synthesis Example 1

5.00 g of TEP-TPA (product name, manufactured by ASAHI YUKIZAI CORPORATION), 7.55 g of N-cyclohexylmaleimide (manufactured by Tokyo Chemical Industry Co., Ltd.) and 4.05 g of methanesulfonic acid as a catalyst were added to 16.75 g of propylene glycol monomethyl ether (hereinafter, abbreviated as PGME in this specification). The mixture was reacted at 140° C. for 7 hours to give a solution containing the reaction product. The solution was diluted with PGME to 30% by mass, and the product was reprecipitated with a methanol/water mixed solvent (200 g). The precipitate obtained was filtered and was dried in a vacuum drier at 60° C. for 24 hours. The target polymer was thus obtained.

GPC analysis of the reaction product indicated that the weight average molecular weight was 11,500 relative to standard polystyrenes. The reaction product obtained is estimated to be a copolymer having a structural unit represented by the following formula (1):

[Chemical Formula 15]

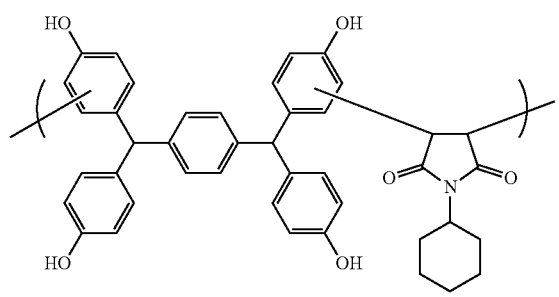

(1)

Synthesis Example 2

7.00 g of TEP-TPA (product name, manufactured by ASAHI YUKIZAI CORPORATION), 7.38 g of N-ethylmaleimide (manufactured by Tokyo Chemical Industry Co., Ltd.) and 2.84 g of methanesulfonic acid as a catalyst were added to 17.22 g of PGME. The mixture was reacted at 140° C. for 7 hours to give a solution containing the reaction product. The solution was diluted with PGME to 30% by mass, and the product was reprecipitated with a methanol/water mixed solvent (200 g, mixing ratio by mass: 50/50). The precipitate obtained was filtered and was dried in a vacuum drier at 60° C. for 24 hours. The target polymer was thus obtained. GPC analysis of the reaction product indicated that the weight average molecular weight was 9,000 relative to standard polystyrenes. The reaction product obtained is estimated to be a copolymer having a structural unit represented by the following formula (2):

[Chemical Formula 16]

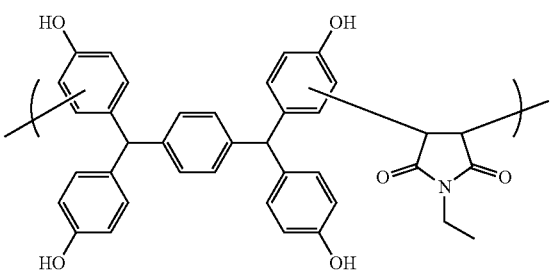

(2)

SYNTHESIS EXAMPLE 3

8.00 g of 2,2'-dihydroxybiphenyl (manufactured by Tokyo Chemical Industry Co., Ltd.), 7.70 g of N-cyclohexylmaleimide (manufactured by Tokyo Chemical Industry Co., Ltd.), 4.13 g of methanesulfonic acid as a catalyst and 0.24 g of hydroquinone as a radical trapping agent were added to 20.06 g of PGME. The mixture was reacted at 140° C. for 20 hours to give a solution containing the reaction product. The solution was diluted with PGME to 30% by mass, and the product was reprecipitated using a methanol/water mixed solvent (600 g, mixing ratio by mass: 50/50). The precipitate obtained was filtered and was dried in a vacuum drier at 60° C. for 24 hours. The target polymer was thus obtained. The polymer was dissolved into PGME to give a 20% by mass solution, to which were added 16.00 g of an anion exchange resin (product name: DOWEX [registered trademark]
MONOSPHERE [registered trademark] 550A, Muromachi Technos Co., Ltd.) and 16.00 g of a cation exchange resin (product name: AMBERLYST [registered trademark] 15JWET, ORGANO CORPORATION). The mixture was stirred at a temperature of 25° C. to 30° C. for 4 hours and was then filtered.

GPC analysis of the reaction product indicated that the weight average molecular weight was 680 relative to standard polystyrenes. The reaction product obtained is estimated to be a copolymer having a structural unit represented by the following formula (3):

[Chemical Formula 17]

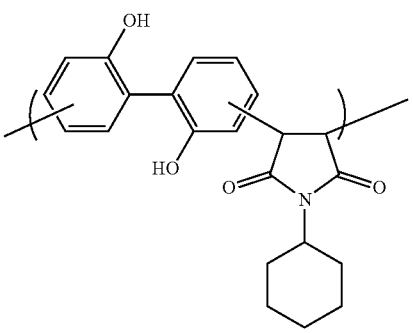

(3)

Synthesis Example 4

8.00 g of diphenylamine (manufactured by Tokyo Chemical Industry Co., Ltd.), 8.47 g of N-cyclohexylmaleimide (manufactured by Tokyo Chemical Industry Co., Ltd.), 4.54 g of methanesulfonic acid as a catalyst and 0.26 g of hydroquinone as a radical trapping agent were added to 21.28 g of PGME. The mixture was reacted at 140° C. for 20 hours to give a solution containing the reaction product. The solution was diluted with PGME to 30% by mass, and the product was reprecipitated using a methanol/water mixed solvent (600 g, mixing ratio by mass: 70/30). The precipitate obtained was filtered and was dried in a vacuum drier at 60° C. for 24 hours. The target polymer was thus obtained.

GPC analysis of the reaction product indicated that the weight average molecular weight was 1,360 relative to standard polystyrenes. The reaction product obtained is estimated to be a copolymer having a structural unit represented by the following formula (4):

[Chemical Formula 18]

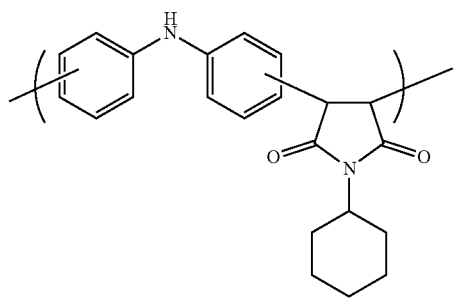

(4)

Synthesis Example 5

50.00 g of N-phenyl-1-naphthylamine (manufactured by Tokyo Chemical Industry Co., Ltd.), 20.43 g of N-cyclohexylmaleimide (manufactured by Tokyo Chemical Industry Co., Ltd.), 21.91 g of methanesulfonic acid as a catalyst and 1.26 g of hydroquinone as a radical trapping agent were added to 167.27 g of propylene glycol monomethyl ether acetate (hereinafter, abbreviated as PGMEA in the present specification). The mixture was reacted at 140° C. for 24 hours to give a solution containing the reaction product. The product was reprecipitated with methanol (2,300 g). The precipitate obtained was filtered and was dried in a vacuum drier at 60° C. for 24 hours. The target polymer was thus obtained. The polymer was dissolved into PGMEA to give a 20% by mass solution, to which were added 70.00 g of an anion exchange resin (product name: DOWEX [registered trademark] MONOSPHERE [registered trademark] 550A, Muromachi Technos Co., Ltd.) and 70.00 g of a cation exchange resin (product name: AMBERLYST [registered trademark] 15JWET, ORGANO CORPORATION). The mixture was stirred at a temperature of 25° C. to 30° C. for 4 hours and was then filtered.

GPC analysis of the reaction product indicated that the weight average molecular weight was 2,000 relative to standard polystyrenes. The reaction product obtained is estimated to be a copolymer having a structural unit represented by the following formula (5):

[Chemical Formula 19]

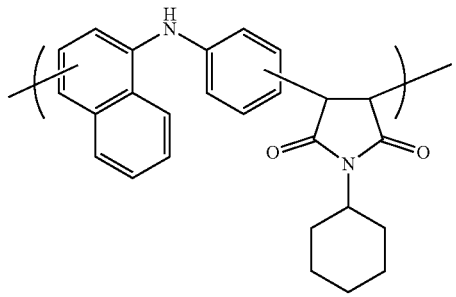

(5)

Synthesis Example 6

15.00 g of carbazole (manufactured by Tokyo Chemical Industry Co., Ltd.), 8.04 g of N-cyclohexylmaleimide (manufactured by Tokyo Chemical Industry Co., Ltd.), 8.62 g of methanesulfonic acid as a catalyst and 0.49 g of hydroquinone as a radical trapping agent were added to 54.91 g of PGME. The mixture was reacted at 140° C. for 23 hours to give a solution containing the reaction product. The product was reprecipitated with methanol (2,800 g). The precipitate obtained was filtered and was dried in a vacuum drier at 60° C. for 24 hours. The target polymer was thus obtained. The polymer was dissolved into PGMEA to give a 20% by mass solution, to which were added 23.00 g of an anion exchange resin (product name: DOWEX [registered trademark] MONOSPHERE [registered trademark] 550A, Muromachi Technos Co., Ltd.) and 23.00 g of a cation exchange resin (product name: AMBERLYST [registered trademark] 15JWET, ORGANO CORPORATION). The mixture was stirred at a temperature of 25° C. to 30° C. for 4 hours and was then filtered.

GPC analysis of the reaction product indicated that the weight average molecular weight was 6,000 relative to standard polystyrenes. The reaction product obtained is estimated to be a copolymer having a structural unit represented by the following formula (6):

[Chemical Formula 20]

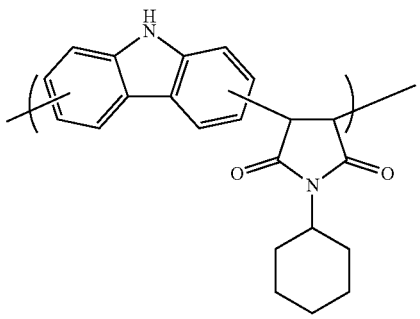

(6)

Synthesis Example 7

50.0 g of ethylcarbazole (manufactured by Tokyo Chemical Industry Co., Ltd.), 24.9 g of maleimide (manufactured by Tokyo Chemical Industry Co., Ltd.), 24.6 g of methanesulfonic acid as a catalyst and 1.41 g of hydroquinone as a radical trapping agent were added to 292 g of PGMEA. The mixture was reacted at 140° C. for 23 hours to give a solution containing the reaction product. The product was reprecipitated with methanol (3,600 g). The precipitate obtained was filtered and was dried in a vacuum drier at 60° C. for 24 hours. The target polymer was thus obtained. The polymer was dissolved into PGMEA to give a 20% by mass solution, to which were added 100.00 g of an anion exchange resin (product name: DOWEX [registered trademark] MONOSPHERE [registered trademark] 550A, Muromachi Technos Co., Ltd.) and 100.00 g of a cation exchange resin (product name: AMBERLYST [registered trademark] 15JWET, ORGANO CORPORATION). The mixture was stirred at a temperature of 25° C. to 30° C. for 4 hours and was then filtered.

GPC analysis of the reaction product indicated that the weight average molecular weight was 1,200 relative to standard polystyrenes. The reaction product obtained is estimated to be a copolymer having a structural unit represented by the following formula (7):

[Chemical Formula 21]

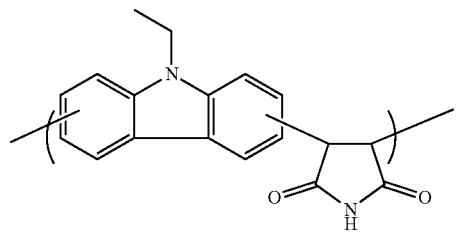

(7)

Comparative Synthesis Example 1

17.67 g of PGMEA, 5.00 g of EHPE-3150 (product name, manufactured by Daicel Corporation), 3.11 g of 9-anthracenecarboxylic acid, 2.09 g of benzoic acid and 0.62 g of ethyltriphenylphosphonium bromide were added to 7.57 g of PGME. The mixture was heated under reflux in a nitrogen atmosphere for 13 hours. To the resultant solution were added 16 g of a cation exchange resin (product name: AMBERLYST [registered trademark] 15JWET, ORGANO CORPORATION) and 16 g of an anion exchange resin (product name: DOWEX [registered trademark] MONOSPHERE [registered trademark] 550A, Muromachi Technos Co., Ltd.). The mixture was stirred at a temperature of 25° C. to 30° C. for 4 hours and was then filtered.

GPC analysis of the reaction product indicated that the weight average molecular weight was 4,700 relative to standard polystyrenes. The reaction product obtained is estimated to be a copolymer having a structural unit represented by the following formula (8):

[Chemical Formula 22]

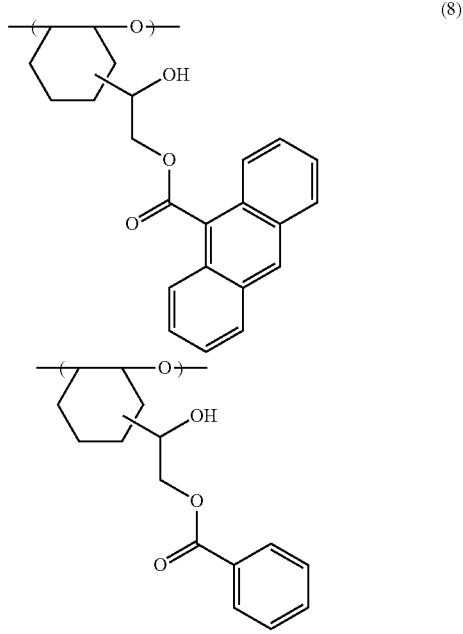

(8)

Preparation of Resist Underlayer Film-Forming Compositions

Example 1

0.80 g of the copolymer obtained in Synthesis Example 1 was mixed together with 6.36 g of PGME, 2.76 g of PGMEA and 0.080 g of a 1% by mass PGME solution of a surfactant (product name: R-30N, manufactured by DIC CORPORATION), thus forming an 8.0% by mass solution. The solution was filtered through a polytetrafluoroethylene microfilter having a pore size of 0.2 μm. A resist underlayer film-forming composition was thus prepared.

Example 2

0.80 g of the copolymer obtained in Synthesis Example 2 was mixed together with 6.36 g of PGME, 2.76 g of PGMEA and 0.080 g of a 1% by mass PGME solution of a surfactant (product name: R-30N, manufactured by DIC CORPORATION), thus forming an 8.0% by mass solution. The solution was filtered through a polytetrafluoroethylene microfilter having a pore size of 0.2 μm. A resist underlayer film-forming composition was thus prepared.

Example 3

2.86 g of a solution containing 0.55 g of the copolymer obtained in Synthesis Example 3 (the solvent was PGME, the same as that used at the time of synthesis, and the solid content was 20.54% by mass) was mixed together with 0.15 g of tetramethoxymethylglycoluril (product name: POWDERLINK [registered trademark] 1174, manufactured by Cytec Industries Incorporated, Japan), 1.47 g of a 1% by mass PGME solution of pyridinium phenolsulfonic acid (manufactured by Midori Kagaku Co., Ltd.), 2.69 g of PGME, 2.78 g of PGMEA and 0.059 g of a 1% by mass PGME solution of a surfactant (product name: R-30N, manufactured by DIC CORPORATION), thus forming a 7.5% by mass solution. The solution was filtered through a polytetrafluoroethylene microfilter having a pore size of 0.2 µm. A resist underlayer film-forming composition was thus prepared.

Example 4

0.55 g of the copolymer obtained in Synthesis Example 4 was mixed together with 0.14 g of tetramethoxymethylglycoluril (product name: POWDERLINK [registered trademark] 1174, manufactured by Cytec Industries Incorporated, Japan), 1.37 g of a 1% by mass PGME solution of pyridinium phenolsulfonic acid (manufactured by Midori Kagaku Co., Ltd.), 5.10 g of PGME, 2.79 g of PGMEA and 0.055 g of a 1% by mass PGME solution of a surfactant (product name: R-30N, manufactured by DIC CORPORATION), thus forming a 7.0% by mass solution. The solution was filtered through a polytetrafluoroethylene microfilter having a pore size of 0.2 µm. A resist underlayer film-forming composition was thus prepared.

Example 5

11.01 g of a solution containing 1.88 g of the copolymer obtained in Synthesis Example 5 (the solvent was PGMEA, and the solid content was 17.08% by mass) was mixed together with 0.47 g of TMOM-BP (product name, the compound of the formula below, manufactured by Honshu Chemical Industry Co., Ltd.), 4.70 g of a 1% by mass PGME solution of pyridinium phenolsulfonic acid (manufactured by Midori Kagaku Co., Ltd.), 10.19 g of PGME, 3.44 g of PGMEA and 0.19 g of a 1% by mass PGME solution of a surfactant (product name: R-30N, manufactured by DIC CORPORATION), thus forming an 8.0% by mass solution. The solution was filtered through a polytetrafluoroethylene microfilter having a pore size of 0.2 µm. A resist underlayer film-forming composition was thus prepared.

[Chemical Formula 23]

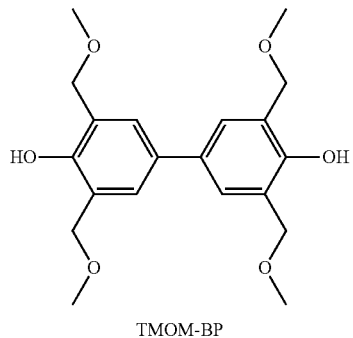

TMOM-BP

Example 6

11.56 g of a solution containing 1.88 g of the copolymer obtained in Synthesis Example 6 (the solvent was PGMEA, and the solid content was 16.27% by mass) was mixed together with 0.47 g of TMOM-BP (product name, manufactured by Honshu Chemical Industry Co., Ltd.), 4.70 g of a 1% by mass PGME solution of pyridinium phenolsulfonic acid (manufactured by Midori Kagaku Co., Ltd.), 9.64 g of PGME, 3.44 g of PGMEA and 0.19 g of a 1% by mass PGME solution of a surfactant (product name: R-30N, manufactured by DIC CORPORATION), thus forming an 8.0% by mass solution. The solution was filtered through a polytetrafluoroethylene microfilter having a pore size of 0.2 µm. A resist underlayer film-forming composition was thus prepared.

Example 7

10.028 g of a solution containing 1.96 g of the copolymer obtained in Synthesis Example 7 (the solvent was PGMEA, and the solid content was 19.60% by mass) was mixed together with 0.39 g of TMOM-BP (product name, manufactured by Honshu Chemical Industry Co., Ltd.), 1.96 g of a 2% by mass PGME solution of TAG2689 (manufactured by King Industries, a thermal acid generator), 6.35 g of PGME, 11.06 g of PGMEA and 0.19 g of a 1% by mass PGMEA solution of a surfactant (product name: R-30N, manufactured by DIC CORPORATION), thus forming an 8.0% by mass solution. The solution was filtered through a polytetrafluoroethylene microfilter having a pore size of 0.2 µm. A resist underlayer film-forming composition was thus prepared.

Comparative Example 1

19.52 g of a solution containing 4.51 g of the copolymer obtained in Comparative Synthesis Example 1 (the solvent was PGME/PGMEA mixed solvent, the same as that used at the time of synthesis, and the solid content was 23.26% by mass) was mixed together with 1.14 g of tetramethoxymethylglycoluril (product name: POWDERLINK [registered trademark] 1174, manufactured by Cytec Industries Incorporated, Japan), 3.41 g of a 1% by mass PGME solution of pyridinium p-toluenesulfonate, 50.68 g of PGME, 14.80 g of PGMEA and 0.45 g of a 1% by mass PGME solution of a surfactant (product name: R-30, manufactured by DIC CORPORATION), thus forming a 6.35% by mass solution. The solution was filtered through a polytetrafluoroethylene microfilter having a pore size of 0.2 µm. A resist underlayer film-forming composition was thus prepared.

Test of Dissolution Into Photoresist Solvents

Each of the resist underlayer film-forming compositions prepared in Examples 1 to 7 and Comparative Example 1 was applied onto a silicon wafer using a spinner. The coating was baked on a hot plate at a temperature shown in Table 1 below for 1 minute to form a resist underlayer film (film thickness: 0.2 µm). The resist underlayer film was immersed in a PGME/PGMEA mixed solvent (mixing ratio by mass: 70/30), which was a solvent used for photoresist solutions, to confirm that the resist underlayer film was insoluble in the solvent. The results are indicated as "○" in Table 1 below.

Test of Optical Parameters

Each of the resist underlayer film-forming compositions prepared in Examples 1 to 7 and Comparative Example 1 was applied onto a silicon wafer using a spinner. The coating was baked on a hot plate at a temperature shown in Table 1 below for 1 minute to form a resist underlayer film (film thickness: 0.2 µm). The resist underlayer films was analyzed with an optical ellipsometer (VUV-VASE VU-302 manufactured by J.A. Woollam) to measure the refractive index (n value) and the attenuation coefficient (k value) at a wavelength of 193 nm. The results are reported in Table 1 below.

To ensure that the resist underlayer films will exhibit a sufficient antireflection function, the k value at a wavelength of 193 nm is desirably 0.1 or above.

Measurement of Dry Etching Rate

Each of the resist underlayer film-forming compositions prepared in Examples 1 to 7 and Comparative Example 1 was applied onto a silicon wafer in the same manner as described above to form a resist underlayer film. The dry etching rates of the resist underlayer film were measured with an RIE system manufactured by Samco Inc., using $CF_4$ as a dry etching gas. The dry etching rates of the resist underlayer film were converted to a relative value, in which the dry etching rate of Comparative Example 1 was taken as 1.00. The results are reported as the "relative dry etching rates" in Table 1 below. The resist underlayer films from each of the resist underlayer film-forming compositions prepared in Examples 1 to 7 had a sufficiently low dry etching rate compared to the dry etching rate of Comparative Example 1. These results indicate that the resist underlayer film-forming compositions used as masks allow for easy processing of substrates.

TABLE 1

| | Baking temperature (deg.C.) | Solvent resistance PGME/PGMEA 70/30 | Optical parameters 193 nm n value | Optical parameters 193 nm k value | Etching resistance | Filling properties | Flatness |
|---|---|---|---|---|---|---|---|
| Example 1 | 350 | ○ | 1.46 | 0.60 | 0.79 | ○ | — |
| Example 2 | 350 | ○ | 1.47 | 0.60 | 0.88 | ○ | — |
| Example 3 | 250 | ○ | 1.50 | 0.53 | 0.87 | ○ | — |
| Example 4 | 250 | ○ | 1.57 | 0.53 | 0.85 | ○ | — |
| Example 5 | 250 | ○ | 1.40 | 0.36 | 0.76 | ○ | ○ |
| Example 6 | 250 | ○ | 1.48 | 0.32 | 0.78 | ○ | — |
| Example 7 | 240 | ○ | 1.51 | 0.32 | 0.71 | ○ | — |
| Comparative Example 1 | 215 | ○ | 1.54 | 0.26 | 1.00 | x | x |

Evaluation of Gap-Filling Properties

Gap-filling properties were evaluated using a 200 nm thick $SOi_2$ substrate that had a dense pattern area consisting of 50 nm wide trenches at 100 nm pitches. Each of the resist underlayer film-forming compositions prepared in Examples 1 to 6 and Comparative Example 1 was applied onto the substrate, and the coating was baked at 250° C. for 60 seconds to form a resist underlayer film having a thickness of about 200 nm. The flatness of the substrates was evaluated using a scanning electron microscope (S-4800) manufactured by Hitachi High-Tech Corporation to confirm whether the resist underlayer film-forming composition had filled the inside of the pattern. As the results, good gap-filling properties were achieved in Examples 1 to 6, but voids were found in Comparative Example 1.

Test of Coatability on Stepped Substrate

To evaluate the coatability on a stepped substrate, the thickness of a coating film formed on a 200 nm thick $SiO_2$ substrate was compared between on a dense pattern area (DENSE) consisting of 50 nm wide trenches at 100 nm pitches and on an open area (OPEN) free from patterns. Each of the resist underlayer film-forming compositions from Example 5 and Comparative Example 1 was applied onto the substrate to form a 150 nm thick film, which was then baked at a predetermined temperature. The coatability onto the stepped substrate was evaluated. Specifically, the film was observed with a scanning electron microscope (S-4800) manufactured by Hitachi High-Tech Corporation to measure the difference in film thickness between on the dense area (the patterned area) and on the open area (the pattern-free area) of the stepped substrate (the difference in level present on the film between the dense area and the open area, called the bias), thereby evaluating the flattening properties. The film thicknesses in the respective areas, and the difference in level present on the film are reported in Table 2. In the evaluation of flatness, the smaller the value of bias, the higher the flattening properties.

TABLE 2

| | DENSE Film thickness (nm) | OPEN Film thickness (nm) | DENSE/OPEN Difference in level (nm) |
|---|---|---|---|
| Example 5 | 91 | 159 | 68 |
| Comparative Example 1 | 70 | 145 | 75 |

INDUSTRIAL APPLICABILITY

The resist underlayer film-forming compositions provided according to the present invention have a high etching resistance and good optical constants, offer a useful dry etching rate ratio, and exhibit a high coatability even on the so-called stepped substrate and can bury the difference in level by forming a flat film having a small variation in film thickness. The present invention also provides polymers suitably used in the resist underlayer film-forming composition, resist underlayer film formed using the resist underlayer film-forming composition, and method for manufacturing a semiconductor device using the resist underlayer film-forming composition.

The invention claimed is:

1. A resist underlayer film-forming composition comprising a solvent and a silicon-free reaction product of a C6-C60 aromatic compound (A) that is at least one member selected from the group consisting of:

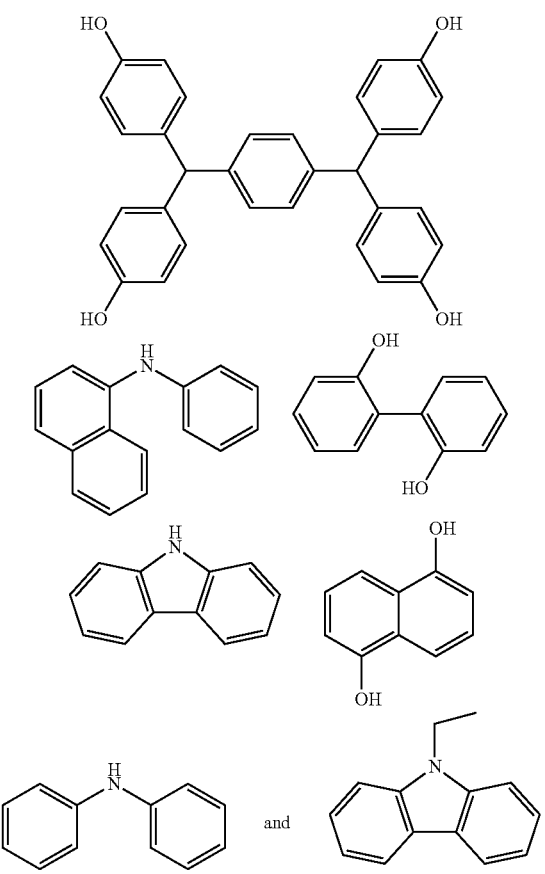

with a compound represented by the following formula (B):

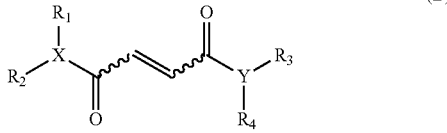

wherein X denotes an oxygen atom or a nitrogen atom,

Y denotes a single bond, an oxygen atom or a nitrogen atom,

X and Y are optionally bonded to each other to form a ring, $R_1$, $R_2$, $R_3$ and $R_4$ each independently denote a hydrogen atom, a C1-C20 alkyl group, a C3-C8 cycloalkyl group or a C6-C10 aromatic group, $R_2$ is present only when X is a nitrogen atom, and $R_4$ is present only when Y is a nitrogen atom, wherein two molecules of the aromatic compound (A) having at least one aromatic ring containing carbon atoms are each connected at one of the carbon atoms of the at least one aromatic ring of the aromatic compound (A) through the two carbon atoms of the carbon-carbon double bond in the compound represented by formula (B).

2. The resist underlayer film-forming composition according to claim 1, wherein X and Y in formula (B) are each an oxygen atom or a nitrogen atom.

3. The resist underlayer film-forming composition according to claim 1, wherein the compound represented by formula (B) is a maleimide derivative represented by the following formula (C):

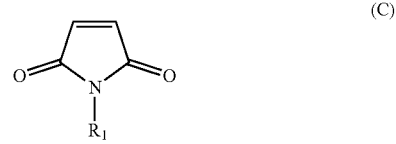

wherein $R_1$ denotes a hydrogen atom, a C1-C20 alkyl group, a C3-C8 cycloalkyl group or a C6-C10 aromatic group.

4. The resist underlayer film-forming composition according to claim 1, further comprising a crosslinking agent.

5. The resist underlayer film-forming composition according to claim 1, further comprising an acid and/or an acid generator.

6. The resist underlayer film-forming composition according to claim 1, wherein the solvent has a boiling point of 160° C. or higher.

7. A resist underlayer film, which is a baked product of a coating film comprising the resist underlayer film-forming composition according to claim 1.

8. A method for manufacturing a semiconductor device, comprising the steps of:

forming on a semiconductor substrate a resist underlayer film using the resist underlayer film-forming composition according to claim 1;

forming a resist film on the resist underlayer film;

forming a resist pattern by irradiating the resist film with light or electron beam followed by development;

forming a patterned resist underlayer film by etching the resist underlayer film through the resist pattern formed above; and processing the semiconductor substrate through the patterned resist underlayer film.

9. A silicon-free copolymer of a C6-C60 aromatic compound (A) and a maleimide derivative represented by the following formula (C):

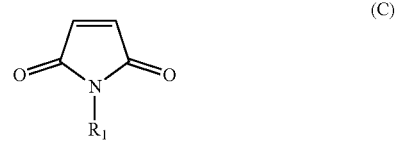

wherein $R_1$ denotes a hydrogen atom, a C1-C20 alkyl group, a C3-C8 cycloalkyl group or a C6-C10 aromatic group, wherein the aromatic compound (A) is at least one member selected from the group consisting of:

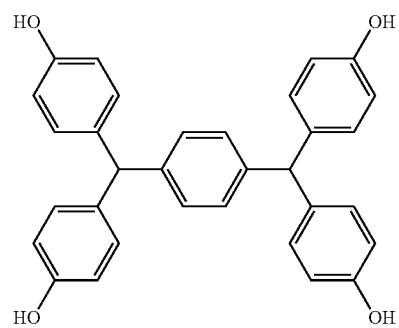
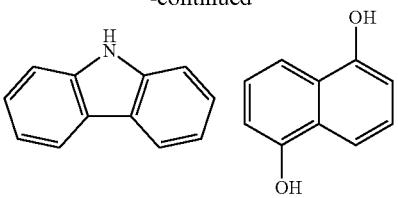
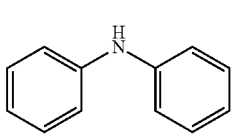
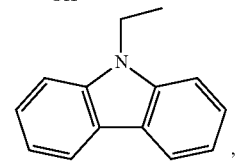
and
wherein in the copolymer, two molecules of the aromatic compound (A) are each connected at one of the carbon atoms of the at least one aromatic ring of the aromatic compound (A) through the two carbon atoms of the carbon-carbon double bond in the maleimide derivative represented by formula (C).
* * * * *